US009938524B2

(12) United States Patent
Fernandez et al.

(10) Patent No.: US 9,938,524 B2
(45) Date of Patent: Apr. 10, 2018

(54) MULTIPLEX ISOLATION OF PROTEIN-ASSOCIATED NUCLEIC ACIDS

(71) Applicant: Active Motif, Inc., Carlsbad, CA (US)

(72) Inventors: Joseph Fernandez, Carlsbad, CA (US); Mary Anne Jelinek, Lake Placid, NY (US); Brian Stanley Egan, Le Mesa, CA (US)

(73) Assignee: Active Motif, Inc., Carlsbad, CA (US)

( * ) Notice: Subject to any disclaimer, the term of this patent is extended or adjusted under 35 U.S.C. 154(b) by 0 days.

(21) Appl. No.: 14/359,877

(22) PCT Filed: Nov. 23, 2012

(86) PCT No.: PCT/US2012/066472
§ 371 (c)(1),
(2) Date: May 21, 2014

(87) PCT Pub. No.: WO2013/078470
PCT Pub. Date: May 30, 2013

(65) Prior Publication Data
US 2015/0111788 A1    Apr. 23, 2015

Related U.S. Application Data

(60) Provisional application No. 61/629,555, filed on Nov. 22, 2011.

(51) Int. Cl.
C12N 15/10 (2006.01)
C07H 21/00 (2006.01)
C40B 50/00 (2006.01)
C40B 40/06 (2006.01)
C12Q 1/68 (2018.01)

(52) U.S. Cl.
CPC ....... C12N 15/1093 (2013.01); C12Q 1/6804 (2013.01)

(58) Field of Classification Search
None
See application file for complete search history.

(56) References Cited

U.S. PATENT DOCUMENTS

| | | | |
|---|---|---|---|
| 6,846,622 B1 * | 1/2005 | Heffron | A61K 39/02 435/29 |
| 2002/0051986 A1 | 5/2002 | Baez et al. | |
| 2005/0130161 A1 * | 6/2005 | Fraser | C12Q 1/6816 435/6.18 |
| 2010/0240101 A1 * | 9/2010 | Lieberman | G01N 33/5308 435/89 |
| 2011/0189677 A1 | 8/2011 | Adli et al. | |
| 2011/0287435 A1 | 11/2011 | Grunenwald et al. | |
| 2013/0011833 A1 * | 1/2013 | Quake | C12Q 1/6804 435/6.11 |
| 2016/0060691 A1 | 3/2016 | Giresi et al. | |

FOREIGN PATENT DOCUMENTS

| | | |
|---|---|---|
| WO | 2004094456 A2 | 11/2004 |
| WO | 2010048605 | 4/2010 |
| WO | 2013078470 A2 | 5/2013 |
| WO | 2017025594 A1 | 2/2017 |

OTHER PUBLICATIONS

Demattei et al "Site-directed integration of transgenes: transposons revisited using DNA-binding-domain technologies" (Genetica, 2010, vol. 138, pp. 531-540).*
Kidder et al In ChIP-Seq: technical considerations for obtaining high-quality data (Nature Immunology vol. 12, No. 10, Oct. 2011, pp. 918-922).*
Hackett et al In "A Transposon and Transposase System for Human Application." (Mol Ther vol. 18, No. 4, pp. 674-683, published online Jan. 26, 2010).*
de Silva Dissertation (2010).*
The Extended European Search Report issued in EP 12852118 dated Apr. 20, 2016.
International Search Report and Written Opinion issued in PCT/US2014/039250 dated Oct. 23, 2014.
Active Motif, I., ChIP-IT Express Magnetic Chromatin Immunoprecipitation Kit. 2011, Active Motif, Carlsbad, California, USA (32 pages).
Alberts et al., Activation of SRF-Regulated Chromosomal Templates by Rho-Family GTPases Requires a Signal that Also Induces H4 Hyperacetylation. Cell. Feb. 20, 1998;92(4):475-487.
Anonymous, ChIP-IT Express Magnetic Chromatin Inmunoprecipitation Kits (version D2) Catalog Nos. 53008 & 53009. Active Motif Product Catalog 2009,:FP-32, XP002755832, (35 pages). Retrieved from the Internet: URL:http://www.biotechniques.com/multimedia/archive/00054/chip-it express manu 54059a.pdf [retrieved on Mar. 21, 2016].
Bertram et al., Integrative elements for Bacillus subtilis yielding tetracycline-dependent growth phenotypes. Nucleic Acids Res. Oct. 12, 2005;33(18):e153 (11 pages).
Braunstein et al., Transcriptional silencing in yeast is associated with reduced nucleosome acetylation. Genes Dev. Apr. 1993;7(4):592-604.
Davies et al., Three-Dimensional Structure of the Tn5 Synaptic Complex Transposition Intermediate. Science. Jul. 7, 2000;289(5476):77-85.
Dirksen and Dawson, Rapid Oxime and Hydrazone Ligations with Aromatic Aldehydes for Biomolecular Labeling. Bioconjug Chem. Dec. 2008;19(12):2543-2548.
Dostie et al., Mapping networks of physical interactions between genomic elements using 5C technology. Nat Protoc. 2007;2(4):988-1002.

(Continued)

*Primary Examiner* — Catherine S Hibbert
(74) *Attorney, Agent, or Firm* — John Storella, P.C.

(57) ABSTRACT

The invention provides novel methods and materials for genetic and genomic analysis using single or multiplex isolation of protein-associated nucleic acids, including transposase-assisted chromatin immunoprecipitation (TAM-ChIP) and antibody-oligonucleotide proximity ligation. These methods comprise tagging and isolating chromatin or other protein-associated nucleic acids and using antibody-oligonucleotide complexes that recognize the proteins associated with such nucleic acids.

24 Claims, 5 Drawing Sheets

(56) References Cited

OTHER PUBLICATIONS

Fredriksson et al., Multiplexed Proximity Ligation Assays to Profile Putative Plasma Biomarkers Relevant to Pancreatic and Ovarian Cancer. Clin Chem. Mar. 2008;54(3):582-589.
Furey, ChIP-seq and beyond: new and improved methodologies to detect and characterize protein-DNA interactions. Nat Rev Genet. Dec. 2012;13(12):840-852.
Gallagher et al., A comprehensive transposon mutant library of Francisella novicida, a bioweapon surrogate. Proc Natl Acad Sci U S A. Jan. 16, 2007;104(3):1009-1014.
Goryshin and Reznikoff, Tn5 in Vitro Transposition. J Biol Chem. Mar. 27, 1998;273(13):7367-7374.
Goryshin et al., Insertional transposon mutagenesis by electroporation of released Tn5 transposition complexes. Nat Biotechnol. Jan. 2000;18(1):97-100.
Goryshin et al., Tn5/IS50 target recognition. Proc Natl Acad Sci U S A. Sep. 1, 1998;95(18):10716-10721.
Grewal and Moazed, Heterochromatin and Epigenetic Control of Gene Expression. Science. Aug. 8, 2003;301(5634):798-802.
Grewal, RNAi-dependent formation of heterochromatin and its diverse functions. Curr Opin Genet Dev. Apr. 2010;20(2):134-141.
Jarvius et al., In Situ Detection of Phosphorylated Platelet-derived Growth Factor Receptor β Using a Generalized Proximity Ligation Method. Mol Cell Proteomics. Sep. 2007;6(9):1500-1509.
Jenuwein and Allis, Translating the Histone Code. Science. Aug. 10, 2010;293(5532):1074-1080.
Jones et al., Methylated DNA and MeCP2 recruit histone deacetylase to repress transcription. Nat Genet. Jun. 1998;19(2):187-191.
Li et al., ChIA-PET tool for comprehensive chromatin interaction analysis with paired-end tag sequencing. Genome Biol. 2010;11(2):R22 (13 pages).
Lieberman-Aiden et al., Comprehensive Mapping of Long-Range Interactions Reveals Folding Principles of the Human Genome. Science. Oct. 9, 2009;326(5950):289-293.
Life Science Tools and Reagents: Global Markets 2011 Apr. 2011, BCC Research, Inc., Wellesley, MA USA. (7 pages).
Luger, et al., Crystal structure of the nucleosome core particle at 2.8 A resolution. Nature. Sep. 18, 1997;389(6648):251-260.
Mahnke Braam and Reznikoff, Functional Characterization of the Tn5 Transposase by Limited Proteolysis. J Biol Chem May 1, 1998;273(18):10908-10913.
Mahnke Braam et al., A Mechanism for Tn5 Inhibition. Carboxyl-Terminal Dimerization. J Biol Chem. Jan. 1, 1999;274(1):86-92.
Rister and Desplan, Deciphering the genome's regulatory code: The many languages of DNA. Bioessays. May 2010;32(5):381-384.
Shi et al., Efficient transposition of preformed synaptic Tn5 complexes in Trypanosoma brucei. Mol Biochem Parasitol. Apr. 30, 2002;121(1):141-144.
Solulink, Protein-Protein Conjugation Kit Solulink Inc.: San Diego. Technical Manual May 29, 2013 accessed online at: http://www.solulink.com/products/ptm/S-9010-1-ProteinProteinConjugationKit.pdf :16 pages.
Steger et al., DOT1L/KMT4 Recruitment and H3K79 Methylation Are Ubiquitously Coupled with Gene Transcription in Mammalian Cells. Mol Cell Biol. Apr. 2008;28(8):2825-2839.
Strahl and Allis, The language of covalent histone modifications. Nature. Jan. 6, 2000;403(6765):41-45.
Suganuma and Workman, Crosstalk among Histone Modifications. Cell. Nov. 14, 2008;135(4):604-607.
Suganuma et al., Tn5 Transposase-Mediated Mouse Transgenesis. Biol Reprod. Dec. 2005;73(6):1157-1163.
Vidal et al., Use of an EZ-Tn5-Based Random Mutagenesis System to Identify a Novel Toxin Regulatory Locus in Clostridium perfringens Strain 13. PLoS One. Jul. 14, 2009;4(7):e6232 (13 pages).
Vire et al., The Polycomb group protein EZH2 directly controls DNA methylation. Nature. Feb. 16, 2006;439(7078):871-874.
Xu et al., A signal-noise model for significance analysis of ChIP-seq with negative control. Bioinformatics. May 1, 2010;26(9):1199-1204.
Zang et al., A clustering approach for identification of enriched domains from histone modification ChIP-Seq data. Bioinformatics. Aug. 1, 2009;25(15):1952-1958.
Zhang et al., Model-based Analysis of ChIP-Seq (MACS). Genome Biol. 2008;9(9):R137 (9 pages).
Buenrostro, J. et al. "Transposition of native chromatin for fast and sensitive epigenomic profiling of open chromatin, DNDNA-binding proteins and nucleosome position." Nature America, Inc. 2013; Nature Methods; Advance Online Publicaiton pp. 1-8.
Akst, Epigenetics Armed German *E.coli*. The Scientist Nov. 2012: 3 pages.
Bruscella et al., The Use of Chromatin Immunoprecipitation to Define . . . J. Bacterial. Oct. 2008; 190(20):6817-6828 (12 pages).
Chu et al. Genomic Maps of Long Noncoding RNA Occupancy . . . Mol. Cell. Nov. 18, 2011;44(4):667-678 (2 pages).
The Extended European Search Report issued in EP 2999784 dated Jan. 18, 2017 (11 pages).
Fang et al., Genome-wide mapping of methylated adenine residues . . . Nat Biotechnol. Dec. 2012;30(12):1232-1239 (8 pages).
Finn et al., Synthesis and Properties of DNA-PNA Chimeric Oligomers, Nucleic Acids Res. Sep. 1, 1996:24(17)3357-3363 (7 pages).
Grewal, RNAi-dependent formation of heterochromatin and its diverse functions. Curr Opin Genet Dev. Apr. 2010; 20 (2); 134-141 (8 pages).
Guttman and Rinn, Modular regulatory principles of large non-coding RNAs. Nature Feb. 15, 2012;482(7385)339-346 (8 pages).
Jones et al., Mammalian chromodomain proteins: their roles in genome organisation and expression: Bioessays. Feb. 2000;22(2):124-137.
Simon et al., The genomic binding sites of a noncoding RNA. PNAS USA Dec. 20, 2011:108(51)20497-20502.
Yandell, Decoding Bacterial Methylomes. The Scientist, May 15, 2013 (5 pages).

* cited by examiner

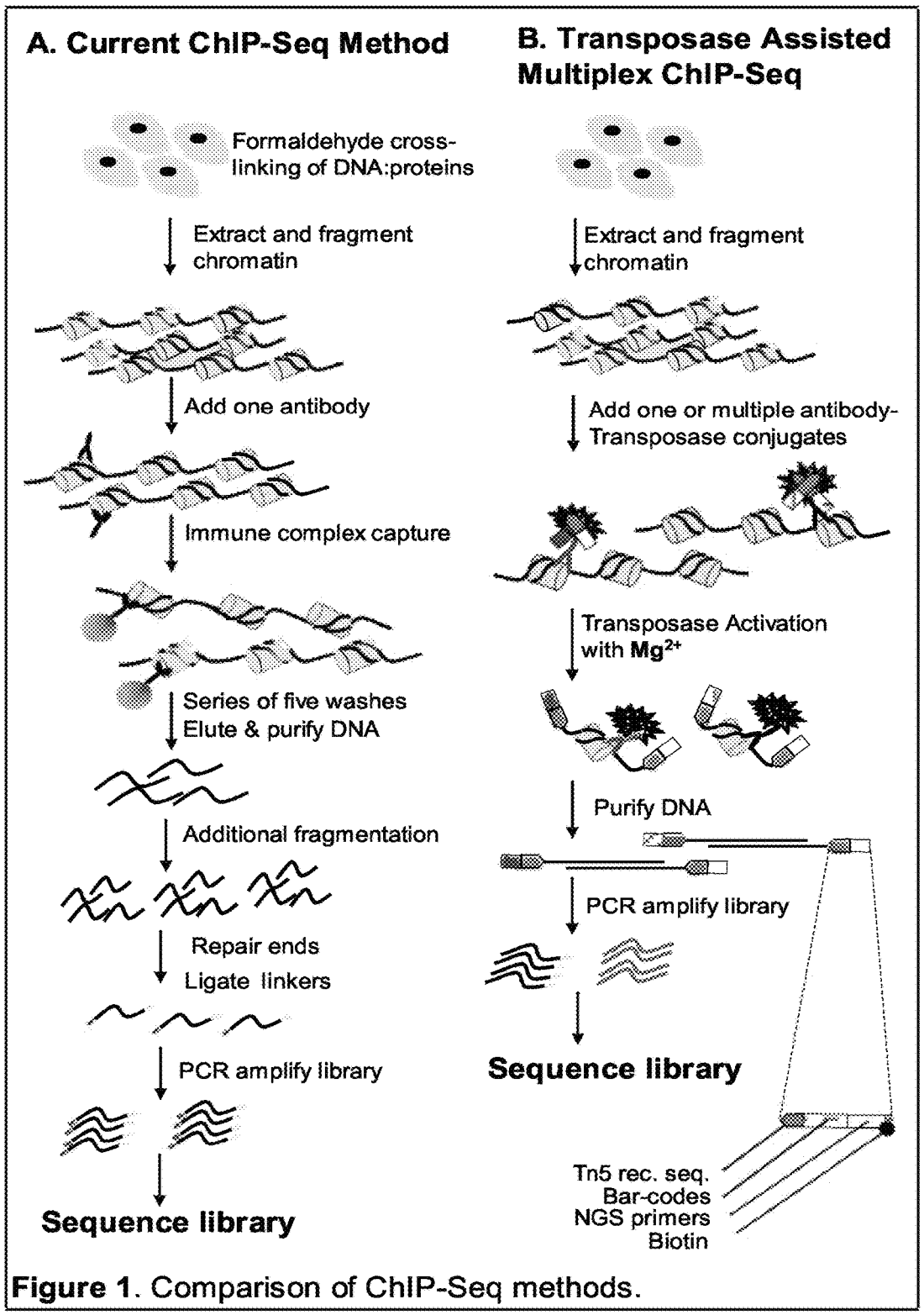
Figure 1. Comparison of ChIP-Seq methods.

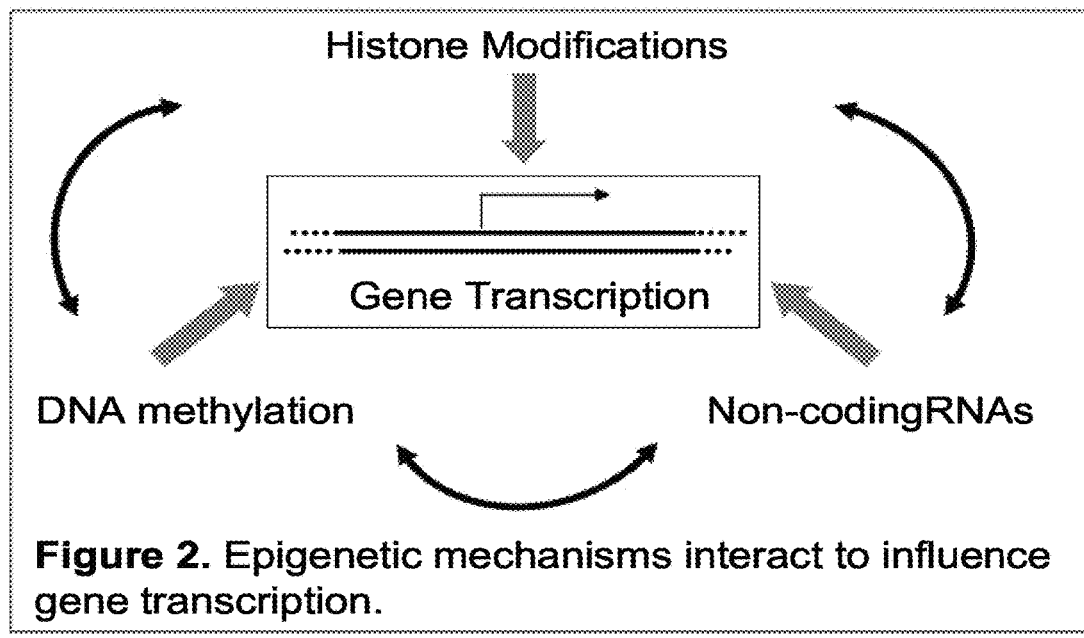
Figure 2. Epigenetic mechanisms interact to influence gene transcription.
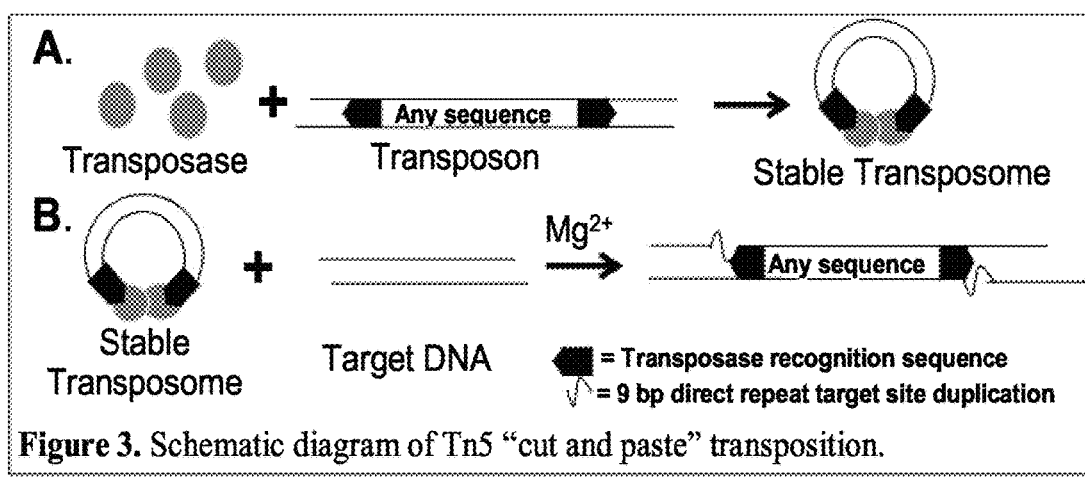
Figure 3. Schematic diagram of Tn5 "cut and paste" transposition.

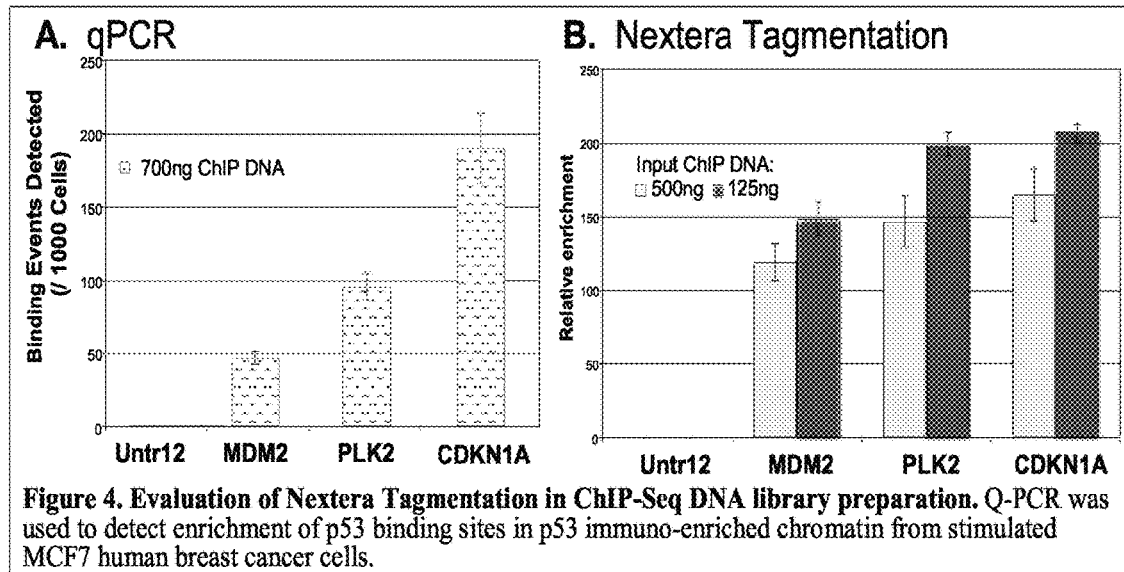
Figure 4. Evaluation of Nextera Tagmentation in ChIP-Seq DNA library preparation. Q-PCR was used to detect enrichment of p53 binding sites in p53 immuno-enriched chromatin from stimulated MCF7 human breast cancer cells.
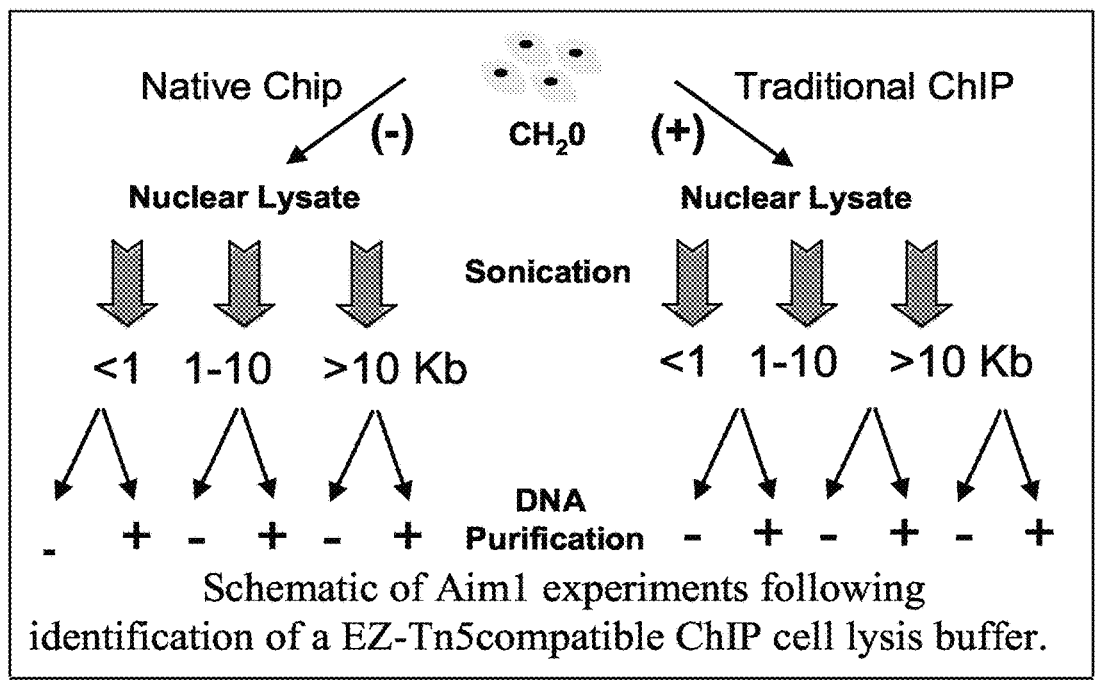
FIGURE 5

SEQUENCE LISTING

<160> NUMBER OF SEQ ID NOS: 2

<210> SEQ ID NO 1
<211> LENGTH: 34
<212> TYPE: DNA
<213> ORGANISM: artificial
<220> FEATURE:
<223> OTHER INFORMATION: One strand of primer 1 in Fig.9

<400> SEQUENCE: 1
actcaatgta tattataggt acgattagcg gatt        34

<210> SEQ ID NO 2

```
<211> LENGTH: 34
<212> TYPE: DNA
<213> ORGANISM: artificial
<220> FEATURE:
<223> OTHER INFORMATION: compliment of SEQ ID NO:1 in Fig. 9 -primer 1

<400> SEQUENCE: 2
tgagttacat ataataccat gctaatccgc ctaa                                34
```

MULTIPLEX ISOLATION OF PROTEIN-ASSOCIATED NUCLEIC ACIDS

CROSS REFERENCE TO RELATED APPLICATIONS

This application is a U.S. national stage filing under 35 U.S.C. § 371 of PCT patent application No. PCT/US2012/066472, filed Nov. 23, 2012, which claims the benefit of priority under 35 U.S.C. § 119(e) to U.S. Provisional Application Ser. No. 61/629,555, filed Nov. 22, 2011, all of which are incorporated by reference herein in their entireties, including all figures.

BACKGROUND OF THE INVENTION

Overview of Epigenetic Mechanisms

Epigenetics is broadly defined as changes in phenotype that are heritable but do not involve changes in the DNA sequence, and, from a historical perspective, stems from long-standing studies of seemingly anomalous (i.e., non-Mendelian) and disparate patterns of inheritance in many organisms [1]. Examples include variation of embryonic growth, mosaic skin coloring, random X inactivation, and plant paramutation. Discoveries in a large number of different model systems have been pivotal in identifying the three principle epigenetic mechanisms of (i) histone modifications, (ii) DNA methylation, and (iii) non-coding RNAs, which function in concert to influence cellular processes such as gene transcription, DNA repair, imprinting, aging, and chromatin structure, as depicted in FIG. 2.

Gene transcription occurs in the context of the nucleosomal structure of chromatin. A nucleosome consists of an octamer of histone proteins (two molecules of each core histone H2A, H2B, H3, and H4) around which is wrapped 147 base pairs (bp) of DNA. Histones are small basic proteins with an unstructured amino-terminal "tail" that are the target of numerous post-translational modifications [2, 3]. Specific histone marks in the fission yeast *Saccheromyces pombe* were demonstrated to be directly operating as activating and repressing signals for gene transcription[4]. Methylation of lysine 4 and acetylation of lysine 9 of histone H3 are associated with transcriptionally active chromatin, while methylation of lysine 20 of histone H4 and methylation of lysine 9 and 27 of histone H3 are repressive marks, found in transcriptionally silent heterochromatin regions [5, 6]. The repressive histone H3 lysine 9 trimethyl-mark is bound by HP1 proteins, which in turn recruit non-coding RNAs involved in regulating heterochromatin formation[7].

Similar mechanistic links have also been identified between histone marks and DNA methylation. Highly repetitive DNA tandem repeat sequences such as those found in pericentric heterochromatin rely on the repressive H3K9 methylation mark to direct de novo DNA methylation while at promoters, EZH2, a histone lysine methyltransferase containing complex is involved [8]. Members of the methyl-CpG binding domain (MBD) family of proteins which are readers of DNA methylation are found in complexes with histone modifying enzymes (MeCP2 recruits histone deacetylases to mediate histone repressive marks [9]). Studies in multicellular organisms such as the invertebrates *Caenorhabditis elegans* and *Drosophila melanogaster* and plants such as *Arabidopsis thaliana* have generated crucial links between these epigenetic mechanisms [10].

In spite of all the advances to date, however, the epigenetics research field is still in the discovery phase, with many mechanistic questions remaining unanswered and many key players yet to be identified. Just as in the past, the continued study of epigenetic mechanisms in a variety of model organisms will be required to answer these questions. Development of enabling technologies suitable for a broad spectrum of model systems are also critical for accelerating the rate of discovery, especially since the various epigenetic mechanisms are functionally interconnected.

Chromatin Immunoprecipitation (ChIP)

ChIP was first described in 1993 following studies of the association of histone acetylation state with transcriptional gene silencing in yeast [11]. Its adaptation to mammalian cells was reported five years later, in 1998 [12]. Since its initial description, the technique has remained essentially unchanged. As described below and depicted in FIG. 1, Panel A, DNA sequence analysis is performed on the fraction of DNA isolated by immunoprecipitation with antibodies specific to the protein of interest. This technique is used in a wide variety of applications. These include profiling histone modification patterns, from their intragenic distribution through to genome-wide analysis, determining the composition of protein complexes recruited by specific histone marks, identifying regions of de novo DNA methylation, or, with some modifications to the procedure, detecting nascent non-coding RNAs.

Advances in PCR and DNA sequencing technologies have positively impacted the DNA analysis portion of the ChIP technique, which has expanded from semi-quantitative analysis of single genes using end-point PCR, to quantitative analysis with real-time PCR, through to genome-wide analysis afforded by ChIP-chip, wherein the captured DNA is used to probe a high-density microarray, or ChIP-Seq, wherein the captured DNA is subjected to NGS ("next generation sequencing") [6, 13]. While these improvements have increased the magnitude of sequence information available for analysis from a single reaction, the limitations associated with efficient immunocapture of protein-associated DNA have not been addressed.

Only incremental improvements, such as the introduction of magnetic beads for immunocapture in place of agarose or sepharose beads, as in Active Motif's ChIP-IT Express™ kit, have been made [14]. The improved recovery (fewer beads are lost during wash steps), reduced background (wash steps are more thorough) afforded through the use of magnetic beads has allowed for a ten-fold reduction in the sample size requirements, from 2-10 million cells to 0.1-1 million cells. In general, these lower sample requirements apply only to high affinity antibodies targeting abundant proteins, such as RNA polymerase II or histone modifications. In addition, the sample size requirement remains a considerable barrier in some research areas, such as embryology and stem cells where cell numbers are very limiting, and is further compounded by the limitation that the only a single protein can be analyzed in each ChIP experiment. The number of cells required is thus directly proportional to the number of proteins to be analyzed, impacting cost and time considerations. An additional challenge stems from the need of ultra-high affinity antibodies for use in this technique. Many antibodies qualified for use in immunofluorescence and/or immunohistochemistry, which can be used to demonstrate in situ association of the protein of interest with DNA or chromatin, or antibodies which have been shown to effectively function in immunoprecipitation, fail in ChIP applications where the target protein is present in high molecular weight multi-protein-chromatin complexes containing DNA fragments up to 1 kb (kilobase) in length. The binding affinity of the antibody for its cognate target must be strong enough to withstand the physical forces associated with constant agitation of the suspension and immobilization by the beads used to isolate the complexes.

Need for and Benefits of the Invention

The instant invention has broad and significant practical applications. These applications span all life sciences research with eukaryotic organisms, because epigenetic mechanisms are highly conserved throughout eukaryotes. The methods of this invention are more efficient than existing methods such as ChIP. These new, patentable methods enable concurrent analysis of multiple chromatin-associated proteins, eliminate the labor intensive NGS library preparation procedures, and have the potential to significantly reduce the amount of samples needed compared to traditional ChIP methods. This is relevant to not only to the stem cell and embryology research fields where samples are limiting, but also fields such as high throughput screening of large numbers of samples in clinical and pharmaceutical applications, where miniaturization is a major cost driver. In addition, ChIP analysis is limited by the small percentage of antibodies that work effectively in the method. Since the methods of the invention do not require immunoprecipitation, antibodies that do not work in ChIP can be adapted to work with the instant invention, thereby expanding the number of cellular proteins whose genomic distribution can now be determined.

SUMMARY OF THE INVENTION

One aspect of the invention concerns methods and reagents for making a nucleic acid sequence library or libraries. Such methods involve extracting and fragmenting chromatin from a prepared sample, adding at least one antibody-oligonucleotide conjugate comprising an extraction moiety, allowing said antibody(ies) to locate at its/their target protein(s) in said chromatin fragments, tagging the nucleic acid in said chromatin fragments with said conjugate by inducing an intermolecular reaction between said oligonucleotide and said nucleic acid, extracting the nucleic acid so tagged using the extraction moiety.

In some embodiments, the antibody-oligonucleotide conjugate further comprises transposase and the intermolecular reaction is transposition, the extraction moiety is a biotin molecule, and/or the intermolecular reaction is selected from the group: transposition, ligation, recombination, hybridization, and topoisomerase-assisted insertion.

A related aspect of the invention concerns antibody-transposome complexes. Such complexes comprise an antibody that binds a target nucleic acid-associated protein conjugated to a transposome that comprises a transposase and a transposon cassette.

Another aspect of the invention relates to methods for performing proximity ligation. Such methods include contacting a cross-linked and fragmented chromatin sample with an antibody-oligonucleotide conjugate under dilute conditions to promote ligation of the ends of the chromatin fragment to the ends of the oligonucleotide of the antibody-oligonucleotide conjugate, wherein the oligonucleotide is double stranded and comprises at least two recognition sites for a freeing restriction enzyme, primer sites for amplification, at least one bar code sequence to identify the conjugated antibody, complementary overhangs to facilitate ligation, and optionally, a spacer for optimizing the length of the oligonucleotide, and then ligating the antibody-oligonucleotide conjugates to the cross-linked and fragmented chromatin sample.

A related aspect involves antibody-oligonucleotide conjugates useful for proximity ligation reactions. These typically comprises an antibody that binds a target nucleic acid-associated protein conjugated to a double-stranded oligonucleotide that comprises at least two recognition sites for a freeing restriction enzyme, primer sites for amplification, at least one bar code sequence to identify the conjugated antibody, complementary overhangs to facilitate ligation, and optionally, a spacer for optimizing the length of the oligonucleotide.

BRIEF DESCRIPTION OF THE FIGURES

FIGS. 1-8 depict various aspects and embodiments of the invention.

DETAILED DESCRIPTION OF THE INVENTION

Figure 6:
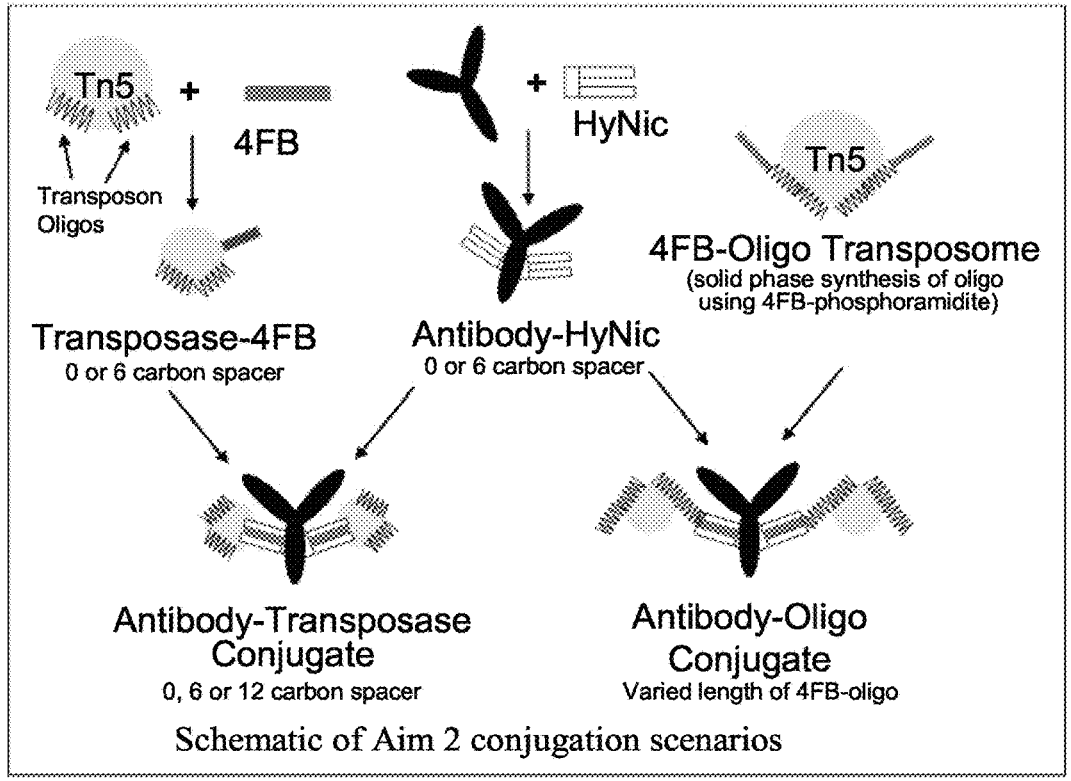

This invention provides methods of tagging and isolating DNA or other nucleic acids that are associated with a protein or proteins of interest. Generally the methods comprise first preparing complexes of oligonucleotide tag(s) or barcode(s) with antibody(ies) that recognize protein(s) of interest in chromatin or that are otherwise associated with nucleic acids. The tagged oligonucleotide complexes may further comprise an extraction moiety, such as a biotin molecule (or other member of a high affinity binding pair), that can be used to extract or isolate the tagged nucleic acid. A "binding partner" or "member" of a high affinity binding pair (i.e., a pair of molecules wherein one of the molecules binds to the second molecule with high affinity (e.g., biotin and avidin (or streptavidin), carbohydrates and lectins, effector and receptor molecules, cofactors and enzymes, enzyme inhibitors and enzymes, and the like).

Next, when the complexes are added to the nucleic acids, the antibody(ies) recognize or bind to the protein(s) of interest that are associated with the nucleic acids. Using a variety of intermolecular reactions, the nucleic acid proximate those proteins is tagged with the complex. Thus, the proximate nucleic acid is tagged with one or more oligonucleotide bar code(s) and, optionally, a moiety that allows for purification or isolation.

One embodiment of the invention, termed "Transposase-Assisted Multi-analyte Chromatin ImmunoPrecipitation" or "TAM-ChIP", is a novel, patentable method that significantly improves ChIP, the principle technique currently used to study how histone post-translational modifications and the proteins which they recruit regulate gene expression. Traditional ChIP is a cumbersome multiday, multistep procedure that requires large numbers of cells, ultra-high affinity antibodies for the immunocapture of large protein-chromatin complexes, and is limited to the analysis of a single protein species per sample.

Briefly, conventional ChIP methods involve the cross-linking of DNA and protein in live cells, isolation of cross-linked material, shearing of DNA (still bound, through cross-linking, to protein), immunoprecipitation of the cross-inked DNA-protein complexes via antibody-binding of the protein of interest (still bound to DNA), reverse-cross-linking of DNA and proteins, and the detection or sequencing of DNA molecules that were cross-linked to the immunoprecipitated DNA-protein complexes, allowing the generation of specific, DNA sequence context data (FIG. 1, Panel A). For ChIP-Seq applications, the elapsed time from formaldehyde cross-linking of cells to sequencing-ready library is typically five days. Relative to the advances made in the understanding the epigenetic mechanisms of DNA methylation and micro- or non-coding RNAs, the limitations of the ChIP technique have significantly hampered the understanding of the biological function of histone modifications.

In contrast, TAM-ChIP (FIG. 1, Panel B) removes a number of technical and sample-size barriers associated with traditional ChIP by eliminating the inefficient immunoprecipitation and labor intensive library preparation steps of the method and bringing high throughput sample processing and multi-analyte capabilities to the ChIP method. TAM-ChIP enables rapid (<24 hour elapsed time) and streamlined analysis of one or several protein-chromatin interactions for analysis of either a single gene all the way through to genome-wide interrogation. To achieve this, antibodies specific for the protein(s) of interest are first conjugated to a transposase:transposon complex (Transposome™) charged with synthetic oligonucleotide(s) that comprise a transposon cassette containing the following features:

Transposase recognition sequences required by the for catalysis of the DNA integration reaction;
a biotin (or other) molecule conjugated to an oligonucleotide, preferably at one end, to facilitate purification of targeted DNA with streptavidin magnetic beads (or other suitable support conjugated to the other member of the selected high affinity binding pair);
unique bar code sequences (i.e., short nucleotide sequences, i.e., from 1-1,000 bases, preferably 1-50 bases, preferably fewer than 20, even more preferably fewer than 10 bases) that uniquely label an oligonucleotide species so that it can be distinguished from other oligonucleotide species in the reaction, and which correspond to a particular antibody) for antibody identification in multi-analyte applications in which multiple antibodies are used simultaneously with the same sample material;
for whole genome sequencing applications, platform-specific tags required for next generation sequencing (NGS).

The antibody-transposase conjugates are incubated with chromatin fragments extracted from isolated cells, tissue, or whole organs (or other cell-containing biological samples) to allow specific antibody-protein binding. The transposase is subsequently activated by addition of a cofactor, e.g., $Mg^{2+}$, after sample dilution to prevent intermolecular events. Transposase activation results in random insertion of the two transposase-associated oligonucleotides into the antibody-associated DNA fragment, thereby producing analysis-ready templates following a deproteination step and capture of biotin-tagged DNA fragments using streptavidin-coated magnetic beads.

Leveraging Tn5 Transposase for Improving ChIP

Transposable elements are discrete DNA segments that can repeatedly insert into a few or many sites in a host genome. Transposition occurs without need for extensive DNA sequence homology or host gene functions required in classical homologous recombination[15]. Consequently, transposable elements have proven to be superb tools for molecular genetics and have been used extensively in vivo to link sequence information to gene function. More recently, in vitro applications have also been developed, specifically for Tn5, a class II "cut and paste" transposable element isolated from gram negative bacteria [16]. Catalysis involves nicking of DNA to generate nucleophilic 3' OH groups on both strands at the ends of the 19 by Tn5 transposase DNA recognition sequence. The 5' ends are also cleaved within the synaptic complex, releasing the transposable element from the donor DNA (FIG. 3, Panel A). This mechanism allows for the formation of a stable complex between the enzyme and transposon in the absence of $Mg^{2+}$ [17], and is the basis for the in vitro transposase technologies developed by Epicentre Biotechnology (Madison, Wis., USA).

Transposases are not conventional enzymes in the classical sense, in that there is no turn-over. Spontaneous product release is not required and consequently the transposase is required in stoicheometric quantities [15].

Tn5-mediated transposition is random, causing a small 9 by duplication of the target sequence immediately adjacent to the insertion site (FIG. 3, Panel B). The result is analogous to using a restriction endonuclease with random sequence specificity that also contains a ligase activity. Epicenter's EZ-Tn5 Transposome™ technology utilizes a transposase-transposon complex which exhibits 1,000 fold greater activity than wild type Tn5, achieved by combining a mutated recombinant Tn5 transposase enzyme with two synthetic oligonucleotides containing optimized 19 by transposase recognition sequence [16, 18], and is the basis of Epicentre's Nextera™ product used to streamline NGS library preparation. Using such a recombinant enzyme (whether naturally occurring or engineered to have improved transposition activity), transposition occurs with at efficiencies of 0.5-5%, using as little as 50 ng of purified DNA, yielding >$10^6$ transpositions per reaction. The transposome is so stable that it can be introduced via electroporation into living organisms, both prokaryotic (Gram negative and Gram positive bacteria [19-22]) and eukaryotic (yeast, trypanosome, and mice [19, 23, 24]) where in the presence of endogenous $Mg^{2+}$, transposon insertion has shown to be random and stable. The ability of the Tn5 transposase to recognize eukaryotic chromatin as a substrate is extremely significant, as it can be adapted to transform ChIP into a multi-analyte method suitable for high through-put applications.

As described above and depicted in FIG. 1, Panel B, TAM-ChIP technology development uses an antibody-transposome linking moiety to effectively conjugate the Transposome™ to a targeting antibody that binds a targeted DNA-associated protein. Binding of the antibody to its target protein in chromatin (or other nucleic acids with which the protein associates in cells under physiological conditions) optimizes transposase activity with chromatin as a DNA substrate. The TAM-ChIP method involves allowing formation of complexes between the antibody-Transposome™ conjugate and chromatin fragments containing the antibody's target protein. The samples are then diluted (to ensure transposition of the olignucleotide payload in the transposon cassette into the same DNA fragment) and the chromatin-associated-transposase activated by the addition of the $Mg^{2+}$ co-factor, resulting in the insertion of the transposon cassette containing bar-code sequences and NGS compatible primer sites into flanking DNA regions (FIG. 1, Panel B). Following DNA purification to remove proteins, PCR amplification (or another suitable amplification process) with primers complementary to the oligonucleotides in the can be performed to generate NGS compatible libraries for sequencing.

The direct insertion of the oligonucleotide duplex in the transposon cassette by the transposase eliminates the need for immunoprecipitation, thereby reducing the input DNA requirement. It can also eliminate the need for ultra-high affinity antibodies, thereby expanding the application of the ChIP technique to a broader range of cellular targets which were previously excluded due to the lack of suitable antibodies. The inclusion of barcode sequences in the oligonucleotides allows for the identification of the corresponding immunoprecipitating antibody, and is the basis of the multi-analyte potential of TAM-ChIP, which for the first time enables simultaneous use of multiple antibodies in the same sample and experiment. This innovation also has the benefits of further reducing sample size requirements and enables elucidation of protein co-association in sequence-specific contexts throughout the genome.

METHODS AND REPRESENTATIVE EXAMPLES

Preferred methods, materials, and conditions for carrying out some preferred, non-limiting, representative embodiments of the invention are described below. Those of ordinary skill in the art will readily appreciate that the invention can be practiced in a number of additional embodiments using equivalent alternate techniques and materials.

Example 1: TAM-ChIP

Preliminary Data

In order to improve the turnaround-time of conventional ChIP-Seq services, Epicentre's Nextera™ DNA Sample Prep kit, which uses the EZ-Tn5 Transposome™ and suppression PCR to generate NGS compatible libraries, was evaluated for suitability for use with ChIP-enriched DNA. ChIP was performed in duplicate using p53 antibodies and 30 µg chromatin extracted from estrogen stimulated MCF-7 cells (a human breast cancer cell line) following established protocols, and isolated DNA was then purified. Quantitative PCR was performed on known p53 binding sites to validate the specificity of the anti-p53 ChIP reactions (FIG. 4, Panel A). Untr12 is a negative control in a gene desert on human chromosome 12 and is not expected to be bound by p53.

The Nextera transposition reaction was performed using two quantities of ChIP DNA (FIG. 4, Panel B) according to the manufacturer's protocol. The DNA libraries were purified and used for PCR according to the Nextera protocol for 18 cycles. The amplified DNA was purified and quantified by measuring absorbance at 260 nm (A260) using a Nano-Drop spectrophotometer. The amount of DNA produced in the Nextera reaction was in the range of what is typically obtained using the Illumina library protocol.

These data demonstrate the suitability of EZ-Tn5 for use with fragmented DNA substrates, and that the p53 binding sites detected in traditional ChIP are preserved and quantifiable in Nextera-generated libraries. Interestingly, a higher amount of DNA was generated in the Nextera reaction with the smaller amount of DNA isolated by ChIP, suggesting that the transposition efficiency was higher and that less input chromatin may be required for ChIP experiments when EZ-Tn5 is incorporated into the methodology.

For the methods described below, the EZ-Tn5 transposome is purchased from Epicentre Biotechnology (Madison, Wis., USA) and ChIP-IT Express™ reagents and protocols are used (Active Motif, Carlsbad, Calif., USA) as the ChIP reagents throughout this example. The end result is an optimized method for the ChIP-validated antibody-transposome conjugates.

The methods below are performed in human HeLa cell lines, which are easily cultured in vitro to produce the necessary quantities of genomic DNA (gDNA) or chromatin required for the experiments described below. While many epigenetic research tools and consumables target researchers using vertibrate animal model systems, largely because this segment is the largest in the epigenetic research tools market, the principle epigenetic mechanisms are conserved throughout vertebrates (including the primary amino acid sequence of histones and the repertoire of post-translational modifications), although those skilled in the art will be able to adapt the reagents and methods of this invention for use with other organisms. Another compelling reason for the use of mammalian cells for the TAM-ChIP technology stems from the complexity of the genome. ChIP is far more challenging in mammalian cells, where genes represent only 1-1.5% of the genome, than in lower eukaryotes where genes represent a much large fraction of the total genome (compare with 70% in S. Cerevisiae).

TABLE 1

Candidate HeLA genomic loci for qPCR analysis of transposition efficiency

| Transcriptionally Active | | | | |
|---|---|---|---|---|
| GAPDH | HOXA10 | EEF1A1 | TUB1C | LDHA |
| RASSF1A | ACTB | PPIB | PABPC1 | RPS18 |
| Transcriptionally Repressed | | | | |
| PTGER3 | HOXD13 | HBB | Untr12 | NGB |
| CFDP1 | Sat2A | MyoD | PAX2 | MYT1 |

Analytic Methods

The majority of the experiments described below require determination of transposition efficiency, and evalution of the distribution (both abundance and range) of DNA fragments generated as a consequence of transposition. Transposition efficiency can be determined using any suitable technique, for example, by quantitative real-time PCR using a StepOnePlus RT-PCR thermocycler (Applied Biosystems) and primers complimentary to a panel of genomic loci known to be either transcriptionally active or repressed in HeLa cells (Table 1, above) [25]. Transposition results in the insertion the biotin-tagged transposon oligonucleotide into the target DNA, enabling isolation of transposon-tagged DNA fragments with streptavidin-coated magnetic beads and subsequent quantitation in triplicate by real time PCR. A five-fold dilution series of fragmented HeLa genomic DNA can be used as standards to generate a quantitation curve. Identical locus-specific PCR primer sets are used for both samples and standards, and transposition efficiency will be calculated as the median of the DNA recovered for all loci. The generation of tagged fragments less than about 200 by is particularly preferred to achieve the necessary resolution of sequence reads in NGS applications. Evaluation of the abundance and range of transposon tagged-DNA fragment sizes produced by transposition events requires, for example, an Agilent 2100 Bioanalyzer, which employs a microfluidics system for electrophoretic determination of size and quantity of DNA fragments in sample volumes of 1-4 µl.

Transposase Tn5 with Chromatin Substrates

The majority of applications developed to date for the in vitro generated transposase-transposon complex use purified DNA as substrate, and the ability of the Tn5 transposase to utilize chromatin as substrate in vivo has been demonstrated. This example identifies the optimal chromatin extraction and fragmentation method and optimal reaction conditions to achieve maximal transposition efficiency. Transposition efficiency is be determined using quantitative real-time PCR to determine the number of integration events using transposon-specific primers.

Cross-linking of associated proteins to DNA with cell permeable chemicals such as formaldehyde is typically the first step performed in ChIP to assure preservation of DNA: protein interactions while the protein of interest is immunoprecipitated. Typically, cells are incubated for 10 minutes in the presence of 1-4% formaldehyde, formaldehyde is quenched by the addition of glycine, and cells lysed. Native ChIP is an alternate method that does not involve chemical cross-linking agents. Whole cell or nuclear lysates are then sonicated to achieve both improved solubilization and fragmentation of chromatin. Nuclear isolation reportedly reduces non-specific binding during the immunoprecipitation phase of the protocol, thereby improving readout signal to noise ratios. The approach described here is used to determine the effects of protein-DNA cross-linking with formaldehyde and chromatin fragmentation on transposase efficiency. Experiments are repeated on three independent occasions, with quantitative real-time PCR performed in triplicate for each condition.

ChIP Buffer Dilution Evaluation

The composition of the buffers used to extract chromatin from cells contain harsh detergents such as sodium dodecylsulfate (SDS) and EDTA to inhibit nuclease activity. First, the extent to which ChIP buffers need to be diluted so as to preserve transposase activity are determined. Epicentre provides two proprietary reaction buffers for the transposition reaction. The low-molecular weight (LMW) and high-molecular weight (HMW) transposase buffers are used to produce fragment libraries of 200-1,000 by and 200-2,000 by respectively. Only the LMW buffer is used herein to achieve the DNA sequence read resolution required for ChIP-Seq. A mock ChIP experiment is performed following the ChIP-IT Express protocol to produce the buffer composition present in the chromatin immunocapture step, the step at which the transposome would be activated by the addition of $Mg^{2+}$ in the TAM-ChIP method. A two-fold dilution series (ranging from 1:2 to 1:32) of this buffer is prepared in Epicentre's LMW buffer and transposase reactions are performed following manufacturer's established protocols with 50 ng DNA. Reactions in which LMW buffer is spiked with increasing amounts of EDTA (5, 10 and 25 mM) serve as negative controls for transposase activity. Unmethylated lambda phage DNA (48.5 kb), and purified fragmented HeLa cell gDNA (>10 kb fragment size), are used as substrates. Integration efficiency and fragment size profiles of tagged-DNA are determined as described above. Transposition efficiency in the various buffers with the various substrates are reported as a percentage relative to the transposase efficiency observed with neat LMW assay buffer and lambda phage DNA. These data are used to identify the minimum dilution factor by which antibody-chromatin complexes should be diluted such that transposase activity (both transposition efficiency and DNA fragment profile) is unaffected by residual detergents and EDTA. The inclusion of purified Hela DNA enables establishment of a baseline reference for transposase activity with mammalian methylated DNA.

Transposition with Chromatin as Target DNA

FIG. 6 summarizes the experimental scheme for the identification of optimal transposition with chromatin substrates. Chromatin is extracted from untreated and cross-linked cells (1% formaldehyde for ten minutes) and DNA quantitated by measuring A260. Mechanical fragmentation of chromatin, for example, by sonication, is performed such that one third of the sample contains fragments <1000 by (as in traditional ChIP), the second third contains fragments ranging between 1,000 and 10,000 bp, while the third sample contains fragments >10,000 bp. Unfragmented genomic DNA is too viscous for effective in vitro manipulations and enzymatic fragmentation does not resolve higher-order chromatin structures, whose presence would undermine interpretation of NGS results, and consequently, neither is preferably used herein.

DNA in one half of each of these samples is purified to enable comparison of transposition efficiency between chromatin and naked DNA. Chromatin samples (unpurified DNA) are diluted in LMW buffer using the minimum dilution factor determined above. 50 ng chromatin (quantitated by A260) and 50 ng purified DNA is used in transposition reactions using any suitable protocol. Transposition with purified lambda phage DNA is used as reference. Transposition efficiency and fragment size is determined as described above. If transposase activity is too low, the experiment is repeated with 200 ng chromatin, or more as required. This method identifies which chromatin preparation results in the production of a population of fragments wherein greater than 40% are less than 200 by in length. This preparation method is used subsequently in embodiments of the TAM-ChIP technology described below.

Example 2: Antibody-Transposase Conjugates

TAM-ChIP requires that the enzymatic activity of the transposase preferably be unaltered, with regards to catalytic rate and randomness of integration sites, when coupled to another protein. Conjugations with various chemistries and cross-linkers of varying length are compared using ChIP validated antibodies. This example generates functional antibody-transposome conjugates.

An extensive number of ChIP-validated antibodies are commercially available or can be developed using conventional antibody production techniques. Here, antibodies to a chromatin associated protein (RNA polymerase II) and a structural chromatin protein, a histone (anti-histone H3 trimethyl-lysine 4 (H3K4tm) mark associated with transcriptionally active chromatin), are conjugated to the EZ-Tn5 transposome using any suitable approach, two of which are described below.

Antibodies can be chemically cross-linked either to the transposase (protein-protein) or to the transposon (protein-DNA) using HydraLink Chemistry (Solulink, San Diego, Calif., USA), which is stoichiometrically more efficient than traditional EDC/NHS chemistries and has been used in the development of PCR-based proximity ligation assays, recognized as the most sensitive assay for protein detection [26-28]. The chemistry involves formation of reaction between an aromatic hydrazine (hydrazinonicotinamide-HyNic) and an aromatic aldehyde (4-formylbenzamide-4FB), yielding a stable bis-arylhydrazone that is UV-traceable, absorbing at 350 nm. Conjugation reaction kinetics can be augmented 10-100 fold in the presence of aniline, leading to conjugation yields of >95%[26].

Conjugations are performed following the manufacturer's established protocols in quantities sufficient for their functional characterization described below and for their subsequent use in the methods described. Both antibody-transposase and antibody-transposon, the transposase-associated oligonucleotide (FIG. 6) conjugates is prepared using varying cross-linker lengths (0, 6 or 12 carbon side-chains) for protein-protein conjugates or transpose oligonucleotides of varying lengths (synthesized with additional 20, 40 or 60 bp), with the 4FB moiety incorporated during solid phase synthesis. Conjugate stoichiometry is determined by measuring absorption of the bis-arylhydrazone crosslinking product at 350 nm which has a molar extinction coefficient of 1600 $M^{-1}$ [29]. Aliquots reserved at each step are used to monitor transposase activity by measuring transposition efficiency with lambda DNA (as above) and retained antibody recognition of antigen by dot blot analysis using established Active Motif protocols. This Example provides isolation of antibody-transposase conjugates with a stoichiometry of greater than or equal to two transposase molecules per antibody molecule in which the function of antibody and transposase is no less than 90% of their unconjugated counterparts. These conjugates are used below for the the TAM-ChIP technology. Methods for conjugation of antibodies to a variety of molecules (enzymes, dyes, oligonucleotides, biotin) are well established and are considered routine. Tn5 transpsosase fusion proteins have been described and are functional[30, 31]. Accordingly, any suitable approach can be adapted for use in the context of this invention.

Example 3: TAM-ChIP Optimization

Examples 1 and 2 above provides the basis for performing TAM-ChIP and demonstrating its benefits relative to traditional ChIP methods. The optimized chromatin extraction and fragmentation procedure above is combined with the antibody-transposome conjugate to perform the TAM-ChIP procedure. A method of comparing the genomic representation of the sequencing libraries produced by TAM-ChIP and traditional ChIP-Seq is also provided. This is done using two steps. The first step involves optimizing sets of conditions with regards to chromatin and antibody-transposase concentrations, optimization of incubation times using transposition the analytic methods describe above as the readout. The second step is a direct comparison of the genomic representation of the DNA libraries produced by TAM-ChIP with that of conventional ChIP-Seq methods.

Figure 7:
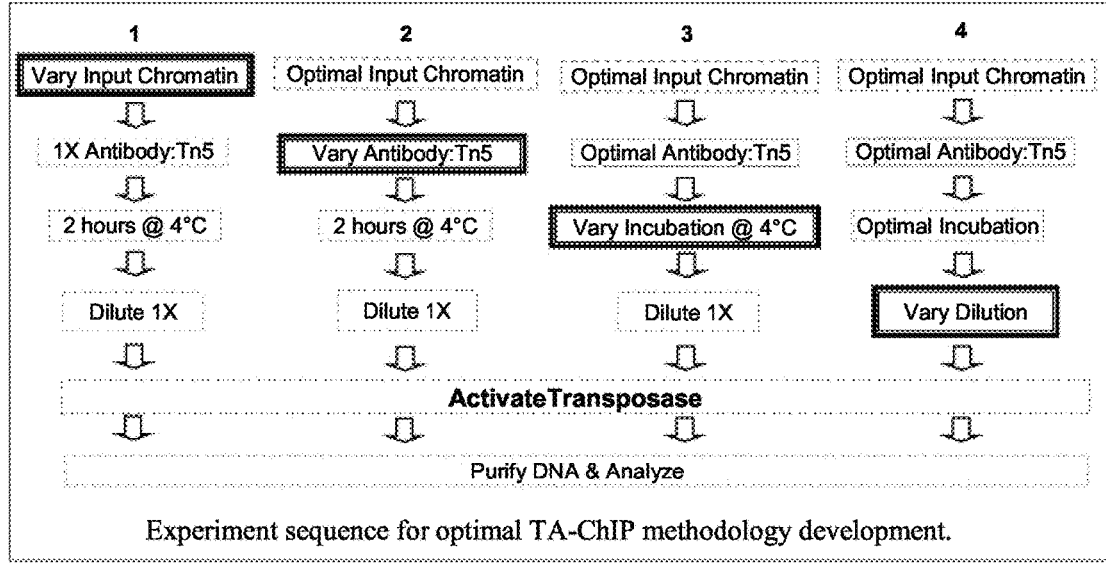

An optimal protocol can be determined using the steps depicted in FIG. 7. First, the optimal amount of chromatin substrate is determined, as this impacts both transposition efficiency and fragment size. Initially, antibody-transposase conjugates are used at a fixed amount, where in the amount of transposase enzyme present corresponds to the amount recommended in applications developed by Epicentre Biotechnology for use with 50 ng DNA.

Triplicate samples of 50, 150, and 450 ng of HeLa cell chromatin (quantitated by A260) are incubated with the antibody-transposase conjugate in 100 µl for two hours at 4° C. (FIG. 7, column 1). The chromatin-antibody complexes are diluted in LMW buffer and transposase activated by the addition of 10 mM Magnesium acetate using the optimized transposase reaction conditions developed above. Samples are be treated with 20 µg Proteinase K for 1 hour at 37° C. and DNA purified using a Zymo DNA Clean & Concentrator-5 Kit (or equivalent). If formaldehyde cross-linked chromatin is used, prior to protease treatment, reversal of cross links is achieved by the addition of an equal volume of Reverse Cross-Linking Buffer (50 mM NaCl in 50 mM Glycine) and samples incubated at 95° C. for 15 min.

Biotin-tagged DNA fragments are captured using streptavidin magnetic beads and transposition efficiency and fragment size profiles are determined as described above. Transposition efficiency is significantly higher at the transcriptionally active genomic targets listed in Table 1 than at the transcriptionally silent regions that are analyzed by qPCR. Consequently, for these experiments transposition efficiency is calculated as a relative ratio of transposition into transcriptionally active and inactive regions, thereby providing a means for comparison of the specificity and efficacy of the antibody-transposome complexes. The range of input chromatin is expanded in subsequent experiments if transposition efficiencies are too low or tagged-DNA fragments too small, the latter a consequence of too little DNA. This set of experiments identifies the antibody-transposome conjugates with optimal activity for chromatin substrates and which chemistry is optimal for the generation of additional antibody-transposase conjugates, such as a non-immune IgG-transposase negative control required for the TAM-ChIP protocol described below.

The optimal conjugate for each of the two antibodies (RNA polyermase II and H3K4tm) is used in the following subsequent experiments (FIG. 7, columns 2 through 4) designed to optimize the effects of different antibody-transposase concentrations, antibody-chromatin incubation times, and sample dilution on transposition efficiency and fragment size. The conditions yielding optimal results are carried forward in the subsequent rounds of procedure optimization. Antibody-transposase concentrations are varied in a two fold dilution series consisting of 2×, 1× and 0.5×; incubations of chromatin with antibody-transposase conjugates are varied for 0.5, 1, 2, and 4 hours; and sample dilution prior to transposase activation to ensure intracomplex transposition are varied as five-fold dilution series (1:x; 1:5x; 1:25x, and 1:125x, where X represents the minimal dilution factor established in Aim 1). The ranges of variables are expanded as warranted based on observed fragment size and transposition efficiency. These experiments identify the conditions which produce a minimum of 500 ng of <200 bp tagged-DNA fragments following 18 cycles of PCR-amounts required for the Illumina sequencing platform. These experiments result in an optimized TAM-ChIP methodology.

Example 4: Validation of NGS Libraries Generated by TAM-ChIP

The DNA libraries produced by the optimized method in developed in the preceding experiments with IgG, RNA polymerase II, and H3K4tm antibody-transposome conjugates are compared with the libraries produced via traditional ChIP-Seq performed with the same unconjugated antibodies. For traditional ChIP-Seq, HeLa chromatin extracts generated for the above set of experiments are incubated with 5 ug antibody for 16 hours at 4° C. 1 ug are left unprocessed and serve as the input control. Antibody-chromatin complexes are captured using protein A coated magnetic beads, washed, eluted, and DNA purified following established procedures. ChIP with 5 ug of non-immune rabbit IgG is performed in parallel as an antibody specificity control. The ChIP-enriched and the untreated sonicated gDNA are processed according standard protocols for library preparation for sequencing in the Illumina Genome Analyzer GAIT. This consists of end-repair, adaptor ligation, size-selection and PCR amplification, and all these steps are done and sequencing performed according to standard methods. The generated data from both TAM-ChIP and traditional ChIP from two independent experiments is analyzed. Reads mapped to the human genome (alignments) are analyzed to find genomic regions with significant enrichments ("peaks") over alignments obtained from either Input or IgG control DNA. Dozens of H3K4tm and RNA Polymerase II ChIP-Seq assays are performed and analyzed, and very similar results are obtained with the peak calling algorithms MACS [32], SICER [33], or CCAT[34]. In addition, software is used to extend the read alignments to the actual length of the DNA fragments (~200-250 bp), and to generate a "signal map" showing alignment ("tag") densities in 32-bp bins across the genome and reproducibility between replicates is typically ~80%. Peaks and signal maps are entered into gene annotation and sample comparison software, returning concise Excel tables showing peak metrics and location of peaks relative to genes. These are used to compare the representation of genomic sequences in the DNA libraries prepared by two methods and show concordance of genomic coverage.

Example 5: Additional TAM ChIP Embodiments

The methods established above will be recognized by those of ordinary skill in the art to be readily carried out in other embodiments, e.g., (a) those comprising antibodies from different animal hosts (rabbit, mouse, rat and goat) specific for proteins associated with either transcriptionally active euchromatin or transcriptionally silenced heterochromatin (i.e. HP1 proteins, and heterochromatin-associated histone marks), (b) TAM-ChIPs wherein antibody-transposase conjugates are be used singly or simultaneously, and with different degrees of complexity (two-plex, three-plex, etc.), including versions with each conjugate bearing a unique bar-code sequence for antibody identification, (c) those where the antibody-oligonucleotide conjugates prepared above are used in a multiple proximity ligation method (see, e.g., Example 6, below). Antibody-oligo conjugates bound to chromatin are diluted, followed by proximity ligation of the antibody-associated oligonucleotide with the associated chromatin fragment end and nicks sealed. Ligation of oligonucleotides to chromatin has been used to map chromatin higher order structures [35], where co-associating chromatin ends in isolated complexes containing higher-order structures are tagged via ligation with primers and then ligated to each other via their proximity, supporting the feasibility of this approach. Use of a reversible antibody-oligonucleotide cross-linking chemistry or the inclusion of a rare restriction endonuclease cleavage site allows libration of the antibody from the DNA now tagged with the bar-code containing oligonucleotide which is then directly amplified for NGS using an appropriate PCR amplification strategy.

Example 6: Antibody-Oligonucleotide Conjugates and Proximity Ligation

Figure 8:
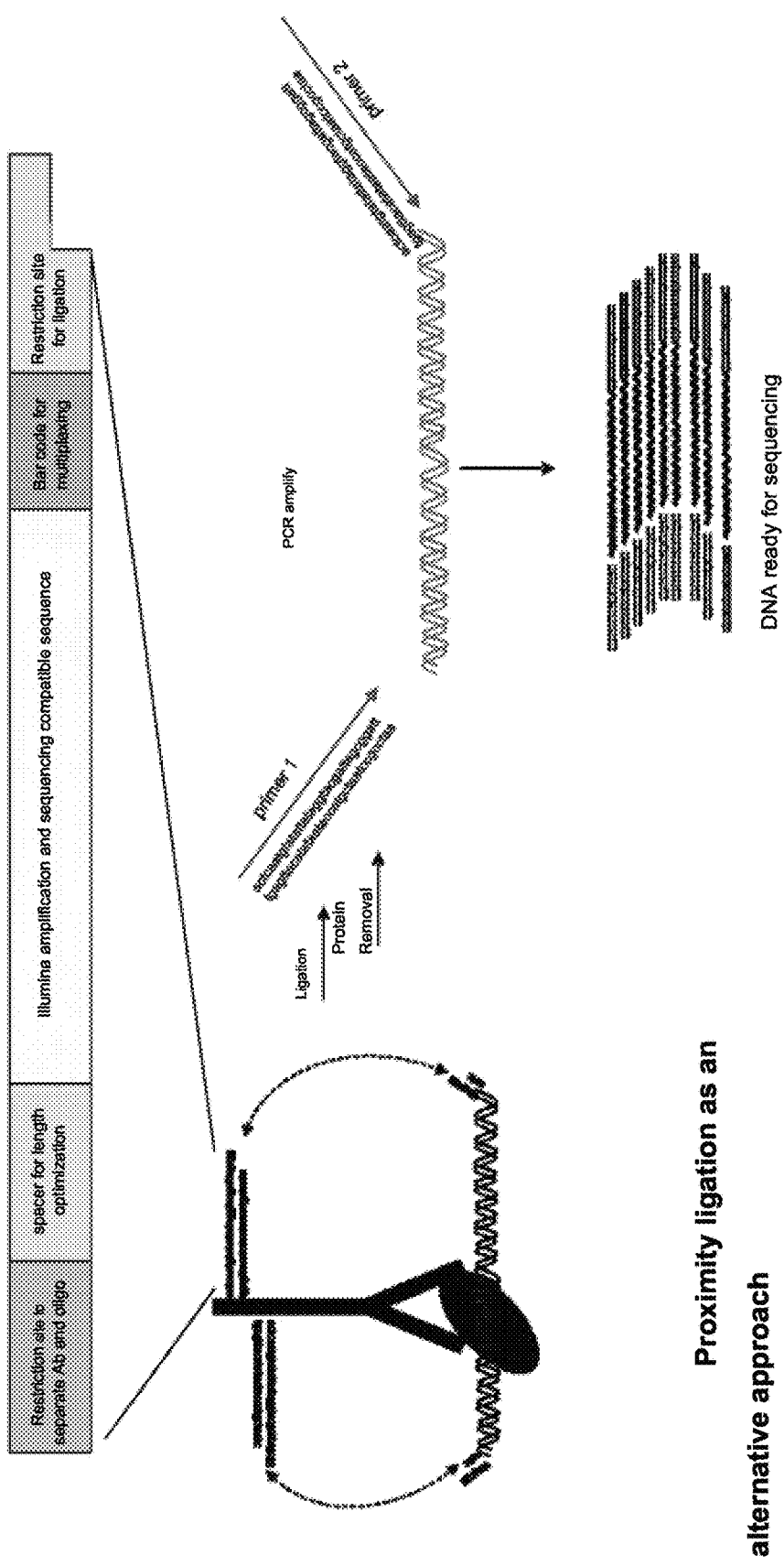

These methods use cross-linked and sonicated (or restriction digested) chromatin as a starting material. Instead of conjugation to transposase, this approach uses conjugation of an antibody to short double-stranded DNA oligonucleotides of known sequence. The conjugate is incubated with cross-linked chromatin that has been either restriction enzyme digested or sonicated, resulting in antibody binding at the intended target. Proximity-mediated ligation is performed, resulting in ligation of the antibody delivered oligos to the target-associated free genomic DNA ends (FIG. 8). Digestion of the cross-linked chromatin and the proximity ligation strategy using sonicated or restriction enzyme digested cross-linked chromatin is well established, and these methods build upon and inventively improve on those used in the 5C and Hi-C technologies (Dostie and Dekker, 2007; Lieberman-Aiden et al., 2009). The key to the ligation is to perform this step under diluted conditions which favor the interaction of DNA molecules held in close proximity. Following ligation, cross-links can be reversed by heating to 65° C. overnight, and proteins can be removed with proteinase K treatment. The regions of interest (e.g., the regions bound by the protein of interest and targeted by the antibody) can be enriched by PCR using primers that anneal to regions within the ligated oligonucleotide sequence, and the resulting amplified DNA can be sequenced using, for example, the Illumina platform, resulting in a genome wide protein binding profile. In addition, this approach is well suited to generate binding profiles of multiple factors in the same sample. This is achieved by designing multiple oligonucleotides, each containing a unique bar code sequence, and conjugating these unique oligos to different antibodies. Multiple antibody conjugates can be added to the same sample at the same time. After sequencing, the data for the multiple targets can be sorted based on the bar code sequence.

Oligonucleotide Embodiments

Several features can be designed into the oligonucleotide(s) that are conjugated to the antibody(ies). These features are listed below and depicted in FIG. 8.
1. The oligonucleotide is double-stranded and the 5' end of one of the strands is linked to biotin (or a member of different high affinity binding pair). The biotin is used for conjugation to the antibody.
2. There is a restriction site (e.g., Not 1, a "freeing" restriction enzyme in the context of the invention) encoded in each oligonucleotide to allow the oligonucleotide to be separated from the antibody, if needed.
3. There is a region of sequence included that functions only for the purpose of varying the oligonucleotide length. The ligation of the oligonucleotide to the free genomic ends of the captured DNA may be dependent on the length of the oligonucleotides. The entire oligonucleotide is typically about 80 nucleotides in length, although longer or shorter lengths may be optimal in a given application.
4. A region is included that is complementary to Illumina (or other suitable) primers. This region facilitates amplification of oligonucleotide-ligated genomic DNA, preferably to be compatible with sequencing on the intended (e.g., Illumina) platform.
5. There is a 4 base pair (or shorter or longer) barcode. Several different oligonucleotides can be synthesized, each having a different bar code. Oligos with different bar codes can be conjugated to different antibodies, thus allowing multiple antibodies to be used in the same reaction.
6. There is a restriction-site-compatible overhang that allows the oligonucleotide to be ligated to restriction-digested genomic DNA. The overhang may preferably be a 4 nucleotide overhang (e.g., GATC, which is compatible with Dpn II, Mbo I, and Sau3A I, digestions). In such cases, the genomic DNA is cut with a restriction enzyme that having a 4 by recognition site, which should on average cleave the DNA every 256 bases. Alternatively, a combination of restriction enzymes having 6 by recognition sites can be used. Alternatively, TA cloning can be used. In such embodiments, sonicated DNA is used which has gone through end repair and A overhang addition. The oligonucleotides are designed to have T overhangs.

Example 7: Alternate Antibody/Oligonucleotide Conjugation Embodiments

Any suitable chemistry can be used to achieve the antibody/oligonucleotide conjugations used in this invention. One such approach is described below.
   1) The biotinylated forward strand oligonucleotide is annealed to the unbiotinylated reverse strand using standard procedures.

2) The antibody can be biotinylated using a number of available kits, for example, the Solulink Chromalink One-Shot biotinylation kit, which allows for quantitation of the number of biotins per antibody and thus allows for optimization of the number of biotins conjugated to the antibody.

3) Self assembly of the conjugate can be achieved by mixing appropriate ratios of the biotinylated oligo, biotinylated antibody, and free streptavidin, a tetramer with four biotin binding sites all of which can be simultaneously occupied.

4) Uncongugated antibody and oligo can be removed using streptavidin magnetic beads.

This approach has been used and validated using a ratio of 2:1:2 (oligo: free streptavidin:antibody). An anti-Goat IgG antibody was coupled to a 100 by oligo by mixing in the presence of free streptavidin. A goat antibody serves as the antigen and was absorbed to maxisorp 96 well plates at different concentrations. The antibody/oligionucleotide conjugate was allowed to bind the antigen and excess antibody was washed away. After washing, signal was detected using PCR with primers that anneal within the conjugated oligonucleotide.

Those of skill in the art will recognize that many equivalent antibody/oligonucleotide conjugation strategies could be substituted for use in the invention. For example, direct via a chemical cross-linker, indirect via other proteins/biomolecules that have strong interactions, including a streptavidin-protein A fusion protein (or protein G). Protein A binds the antibody in a manner that is known not to interfere with antibody function. A single protein A/G immunoglobulin binding domain could be also used, and expressed as a fusion protein. This would then bind with biotinylated oligonucleotides. There are also biotin-binding peptides that are much smaller than the streptavidin protein.

REFERENCES CITED

1. Allis, et al., *Overview and Concepts*, in *Epigenetics*, Allis, et al., Eds. 2006, Cold Spring Harbor Laboratory Press: New York. p. 23-62.
2. Luger, et al., Nature, 1997. 389(6648): p. 251-60.
3. Strahl and Allis, Nature, 2000. 403(6765): p. 41-5.
4. Grewal and D. Moazed, Science, 2003. 301(5634): p. 798-802.
5. Jenuwein and Allis, Science, 2001. 293(5532): p. 1074-80.
6. Suganuma and Workman, Cell, 2008. 135(4): p. 604-7.
7. Grewal, S. I., Current Opinions in Genetics & Development, 2010. 20(2): p. 134-41.
8. Vire, et al., Nature, 2006. 439(7078): p. 871-4.
9. Jones, et al., Nature Genetics, 1998. 19(2): p. 187-91.
10. Felsenfeld, G., *A Brief History of Epigenetics*, in *Epigenetics*, Allis, et al., Eds. 2006, above, p. 15-22.
11. Braunstein, et al., Genes & Development, 1993. 7(4): p. 592-604.
12. Alberts, et al., Cell, 1998. 92(4): p. 475-87.
13. Rister and Desplan, Bioessays, 2010. 32(5): p. 381-4.
14. Active Motif, I., *ChIP-IT Express Magnetic Chromatin Immunoprecipitation Kit*. 2011, Active Motif, Carlsbad, Calif., USA.
15. Mizuucki and Baker, *Chemical Mechansims for Mobilizing DNA*, in *Mobile DNA II*, Craig, et al., Eds. 2002, ASM Press: Washington, p. 12-23.
16. Goryshin and Reznikoff, Journal of Biological Chemistry, 1998. 273(13): p. 7367-74.
17. Davies, et al., Science, 2000. 289(5476): p. 77-85.
18. Goryshin, et al., PNAS USA, 1998. 95(18): p. 10716-21.
19. Goryshin, et al., Nature Biotechnology, 2000. 18(1): p. 97-100.
20. Gallagher, et al., PNAS USA, 2007. 104(3): p. 1009-14.
21. Vidal, et al., PLoS One, 2009. 4(7): p. e6232.
22. Bertram, et al., Nucleic Acids Research, 2005. 33(18): p. e153.
23. Shi, et al., Molecular and Biochemical Parasitology, 2002. 121(1): p. 141-4.
24. Suganuma, et al., Biology of Reproduction, 2005. 73(6): p. 1157-63.
25. Steger, et al., Molecular and Cellular Biology, 2008. 28(8): p. 2825-39.
26. Dirksen and Dawson, Bioconjugate Chemistry, 2008. 19(12): p. 2543-8.
27. Fredriksson, et al., Clinical Chemistry, 2008. 54(3): p. 582-9.
28. Jarvius, et al., Molecular and Cellular Proteomics, 2007. 6(9): p. 1500-9.
29. Solulink, *Protein-Protein Conjugation Kit* Solulink Inc.: San Diego.
30. Mahnke Braam and Reznikoff, Journal of Biological Chemistry, 1998. 273(18): p. 10908-13.
31. Mahnke Braam, et al., Journal of Biological Chemistry, 1999. 274(1): p. 86-92.
32. Zhang, et al., Genome Biol, 2008. 9(9): p. R137.
33. Zang, et al., Bioinformatics, 2009. 25(15): p. 1952-8.
34. Xu, et al., Bioinformatics, 2010. 26(9): p. 1199-204.
35. Li, et al., Genome Biology, 2010. 11(2): p. R22.
36. *Life Science Tools and Reagents: Global Markets* 2011. 2011, BCC Research, Inc., Wellesley, MAm USA.
37. *Epigenetics Market Trends* 2011. 2011, Select BioSciences, Ltd, Sudbury, UK.

We claim:

1. An antibody-oligonucleotide complex, comprising an antibody covalently conjugated to a transposase:transposon complex that comprises a transposase complexed with a transposon cassette, wherein:
   (i) the antibody binds to a target protein in chromatin; and
   (ii) the transposon cassette comprises:
      (1) transposase recognition sequences required for catalysis of a DNA integration reaction;
      (2) one or more oligonucleotide bar code sequences to uniquely identify the conjugated antibody; and
      (3) an extraction moiety.

2. The antibody-oligonucleotide complex of claim 1, wherein the transposon is Tn5.

3. The antibody-oligonucleotide complex of claim 1, wherein the target protein is a histone or a polymerase.

4. The antibody-oligonucleotide complex of claim 1, wherein the oligonucleotide is double stranded and comprises at least two recognition sites for a freeing restriction enzyme.

5. The antibody-oligonucleotide complex of claim 1, wherein the oligonucleotide bar code sequences are fewer than 20 bases.

6. The antibody-oligonucleotide complex of claim 1, wherein the extraction moiety is biotin, avidin or streptavidin.

7. The antibody-oligonucleotide complex of claim 1, wherein the transposon cassette further comprises primer sites for amplification.

8. The antibody-oligonucleotide complex of claim 1, wherein the transposon cassette further comprises platform-specific tags required for next generation sequencing (NGS).

9. A method for tagging chromatin comprising:
   a. providing chromatin from a sample;
   b. adding to the provided chromatin, an antibody-oligonucleotide complex comprising an antibody covalently conjugated to a transposase:transposon complex containing a transposase complexed with a transposon cassette, to create a reaction mixture, wherein:
      (i) the antibody binds to a target protein in the chromatin; and
      (ii) the transposon cassette comprises:
         (1) transposase recognition sequences required for catalysis of a DNA integration reaction;
         (2) one or more oligonucleotide bar code sequences to uniquely identify the conjugated antibody; and
         (3) an extraction moiety;
   c. allowing said antibody from step (b) to bind its target in said chromatin in said reaction mixture;
   d. activating transposase-mediated transposition of the transposon cassette into DNA of the chromatin to tag the chromatin; and
   e. extracting the tagged DNA from step d using the extraction moiety of step b.

10. The method according to claim 9 wherein the transposase:transposon complex further comprises more than one oligonucleotide bar code sequence.

11. The method according to claim 9 wherein the extraction moiety is a biotin molecule.

12. The method according to claim 9 wherein transposition is activated by the addition of a cofactor.

13. The method according to claim 12 wherein the cofactor is $Mg^{2+}$.

14. The method according to claim 9 wherein the chromatin in step (a) is cross-linked.

15. The method according to claim 9 wherein the transposition reaction is performed under dilute conditions.

16. The method according to claim 14 further comprising removing the cross-links after the transposition reaction.

17. The method according to claim 15 further comprising enriching regions bound by protein targeted by the antibody using polymerase chain reaction (PCR).

18. The method according to claim 9, wherein the transposon recognition sequences comprise Tn5 transposase DNA recognition sequences.

19. The method of claim 9, comprising adding to the reaction mixture a plurality of the antibody-oligonucleotide complexes, wherein each complex comprises an antibody against a different target protein and each complex comprises a different bar code sequence to uniquely identify the antibody of the complex.

20. The method of claim 19, further comprising:
   f. sequencing DNA in the chromatin fragments extracted in step e; and
   g. using bar code sequence for the identification of the covalently conjugated antibody.

21. The method of claim 9, wherein the chromatin of step (a) is fragmented.

22. The method of claim 9, wherein the chromatin of step (a) is cross-linked and fragmented.

23. The method of claim 22, comprising adding to the reaction mixture a plurality of the antibody-oligonucleotide complexes, wherein each complex comprises an antibody against a different target protein and each complex comprises a different bar code sequence to uniquely identify the antibody of the complex.

24. The method of claim 23, further comprising:
   f. sequencing DNA in the chromatin fragments extracted in step e; and
   g. using bar code sequence for the identification of the covalently conjugated antibody.

* * * * *